(12) United States Patent
Sung et al.

(10) Patent No.: US 6,245,536 B1
(45) Date of Patent: Jun. 12, 2001

(54) **PROCESS FOR PREPARING ISOFLAVONE AGLUCONE USING *RHODOTORULA GLUTINIS* HAVING AN ABILITY TO PRODUCE ISOFLAVONE AGLUCONE**

(75) Inventors: Tae Kyung Sung, Seoul; Koon Sig Park, Ansan; Beom Hwan Kim, Suwon; Se Cheon An, Ansan; Kil Young Choi, Euiwang; Moo Hoe Doh, Seoul, all of (KR)

(73) Assignee: Shin Dongbang Corporation, Seoul (KR)

( * ) Notice: Subject to any disclaimer, the term of this patent is extended or adjusted under 35 U.S.C. 154(b) by 0 days.

(21) Appl. No.: 09/566,355

(22) Filed: May 8, 2000

(30) Foreign Application Priority Data

Oct. 30, 1999 (KR) .................................................. 99-47744

(51) Int. Cl.$^7$ .............................. C12P 17/06; C12N 1/12; C12N 1/20; C12N 1/16; C12N 1/18
(52) U.S. Cl. ....................... 435/125; 435/125; 435/254.1; 435/254.2; 435/255.1; 435/911
(58) Field of Search ................................. 435/95, 96, 125, 435/252, 252.3, 254.1, 254.2, 255.1, 255.2

(56) References Cited

U.S. PATENT DOCUMENTS

| | | | |
|---|---|---|---|
| 4,874,695 | * | 10/1989 | Pincus . |
| 5,554,519 | * | 9/1996 | Weber et al. . |
| 5,851,792 | * | 12/1998 | Shen et al. . |

* cited by examiner

*Primary Examiner*—Leon B. Lankford, Jr.
*Assistant Examiner*—Michele Flood
(74) *Attorney, Agent, or Firm*—Gardner, Carton & Douglas

(57) ABSTRACT

The present invention relates to a process for preparing isoflavone aglucone using *Rhodotorula glutinis*, more specifically, to a novel *Rhodotorula glutinis* strain (KCCM-10172) which can be isolated from fermented soybeans and has a good ability to convert into isolfavone aglucone, and a process for preparing isoflavone aglucone using the said strain which comprises culture for 30–54 hours in a condition of pH 4.0–8.0 and 25–35° C. using an extract from soybeans or germs of soybeans as a medium and control of content of dissolved oxygen to produce isoflavone containing aglucone of a purity of 90% or more.

5 Claims, No Drawings

PROCESS FOR PREPARING ISOFLAVONE AGLUCONE USING *RHODOTORULA GLUTINIS* HAVING AN ABILITY TO PRODUCE ISOFLAVONE AGLUCONE

FIELD OF THE INVENTION

The present invention relates to a process for preparing isoflavone aglucone using *Rhodotorula glutinis* having an ability to produce isoflavone aglucone. More specifically, it relates to a process for preparing isoflavone aglucone using *Rhodotorula glutinis* (deposited with the Korean Culture Center of Micro-organisms (KCCM), 361-221, Yurim B/D Hongje-1-dong, Seodaemun-gu, Seoul 120–091, Republic of Korea, as deposition No. KCCM-10172 on Oct. 1, 1999) isolated from fermented soybeans and having an ability to produce isolfavone aglucone which comprises culture in a medium using an extract from soybeans or germs of soybeans to produce isoflavone aglucone of a high purity.

BACKGROUND OF THE INVENTION

During the 1950's, many studies on abundant nutritive components of beans and cultivation of beans were actively carried out, and isoflavone contained in soybeans was recently received attention as a functional substance.

Soybean isoflavone is called a vegetable estrogen since it plays a role as an estrogen, a female sex hormone. It has a preventive effect on hypertension, osteoporosis, breast cancer, prostate cancer and a menopausal disorder. That is, soybean isoflavone inhibits a release of calcium from bones of a woman to inhibit a decrease in bone density, which results in a preventive effect on osteoporosis. While breast cancer cells require estrogens, genistein contained in soybeans shows an anti-estrogenic activity in women before the menopause and reduces activities of estrogens associated with breast cancer via hormones and cell metabolism, which results in a preventive effect on breast cancer. On the other hand, a death rate of Japanese people suffering from prostate cancer is very low compared to that of occidentals. It has been reported that the said difference was resulted from different intake of foods made of soybeans. Also, it has been reported from an animal experiment that intake of soybeans inhibited the advance of symptoms of prostate cancer and growth of prostate tumour. Since production of estrogens, a female sex hormone is suppressed during the menopause, women may suffer from a headache, arthralgia and unstableness of body temperature. However, isoflavone reduces symptoms of a menopausal disorder since it shows a weak estrogenic activity.

Isoflavones composed of genistein, glycitein, daidzein, and their glucosides and derivatives are contained in soybeans. While most of them exist in the form of glucosides such as genistin and daidzein, some of them exist in the form of aglucones such as genistein and daidzein due to hydrolysis of carbohydrate residues by β-glucosidase during microbial fermentation and enzyme reaction. The said isoflavone glucosides and aglucones are absorbed within the intestines. Since an absorption rate of aglucones converted by fermentation or enzyme reaction is much higher than that of glucosides, it has been known that isoflavone aglucone contained in fermented foods has an advantage in a view of utility value, compared with isoflavone contained in non-fermented foods.

In general, it has been revealed that aglucone is contained in a ratio of 10% and less in non-fermented foods and in a ratio of 70–80% in fermented foods such as soybean paste and fermented soybeans. Micro-organisms known to hydrolyse isoflavone glucosides up to now are *Bifidobacterium longum, Lactobacillus bulgaricus, Aspergillus niger* and *Sacchoromyces*, and have a common feature that they produce β-glucosidase.

It has been reported that isoflavone in the form of isoflavone aglucone prepared by removing glucoside from isoflavone glycoside was hydrolyzed during fermentation using *Lactobacillus debrueckii* (see: Korean Journal of Food Science 3(1):185–195(1999)). In addition, U.S. Pat. No. 5,554,519 discloses a process for preparing genistein isoflavone which comprises fermentation using *Saccharopolyspora erythraea* and extraction of genistein isoflavone with organic solvent in a condition of pH 8–11, and a Japanese patent laid-open publication No. 60-199396 discloses a process for preparing isoflavone derivatives, daidzein and tectorigenin which comprises fermentation of Streptovertidilium Sp. K-251. A Japanese patent laid-open publication No. 50-160483 discloses that *Aspergillus niger* is cultured aerobically in a medium including potato starch, glucose and soybean for 5 days at 27° C. to produce isoflavone active in vivo, and a Japanese patent laid-open publication No. 50-35393 discloses that *Actinomyces roseolus* is cultured in a medium including soybean, glucose and starch in a neutral condition to produce isoflavone inhibiting catechol-O-methyl transferase activities. In processes using enzymes, esterase, pectinase and cellulase as well as β-glucosidase have been used to hydrolyse glucosides to convert into isoflavone aglucone. For example, WO 9510512 discloses a process for preparing vegetable whey abundant in isoflavone aglucone by hydrolysing isoflavone glucosides with β-glucosidase, esterase or acid. The said enzymes show different conversion ratios according to substrates.

SUMMARY OF THE INVENTION

The present inventors have researched various micro-organisms extensively to discover that *Rhodotorula glutinis*, a micro-organism completely different from the said micro-organisms can hydrolyse isoflavone glucosides effectively to produce isoflavone aglucone in a high yield and a high productivity.

A primary objective of the invention is, therefore, to provide a process for preparing isoflavone aglucone from soybeans or germs of soybeans in a high yield and high productivity using *Rhodotorula glutinis*.

The other objective of the invention is to provide a novel *Rhodotorula glutinis* (KCCM-10172) having an ability to produce isoflavone aglucone.

The process for preparing isoflavone aglucone of the invention to accomplish the said objective comprises use of an extract of soybeans or germs of soybeans as a nutrient and substrate of *Rhodotorula glutinis*, and culture of *Rhodotorula glutinis*.

DETAILED DESCRIPTION OF THE INVENTION

*Rhodotorula glutinis* has been generally known to be an uneconomical micro-organism since it was reported to be a causative agent of putrefaction of fruits such as apples and pears, and a very unusual causative agent of peritonitis in an ambulatory peritoneal dialysis patient (see: Korean Journal of Nephrology, 11(1):85–87(1992)). However, in the present invention, it was found from the investigations on productivity of isoflavone aglucone that *Rhodotorula glutinis* isolated from fermented soybeans showed an ability to convert into isoflavone aglucone, which was not behind those of the conventional micro-organisms. Based on the data, an experiment using the conventional *Rhodotorula glutinis* was carried out, and as a result, it was revealed that it showed a good ability to convert into isoflavone aglucone.

Screening was carried out by grinding fermented soybeans collected in Ilwon, Kyunggi-Do of Korea, diluting the samples with sterile distilled water in a 10 or 100-fold, plating the diluent on a potato dextrose agar medium, and culturing at 30° C. Primary screening was carried out by selecting strains whose growth rates were high and morphological characteristics were different. The selected micro-organisms were cultured on plates (extract, agar 1.5%) including extracts of soybeans or germs of soybeans for secondary screening. The micro-organisms thus selected were thirdly screened to select a strain having a good ability to convert into isoflavone and a high productivity.

Identification of the strain thus selected was committed to Korea Research Institute of Bioscience and Biotechnology (KRIBB) to identify it as a *Rhodotorula glutinis* strain, and deposited with the Korean Culture Center of Microorganisms (KCCM), an international depositary authority as deposition No. KCCM-10172.

In accordance with the invention, a potato dextrose medium was used for seed culture of *Rhodotorula glutinis* isolated from fermented soybeans, and an extract from soybeans or germs of soybeans was used for fermentation in a flask.

In this connection, the extract from soybeans or germs of soybeans may be an extract from soybeans or germs of soybeans used conventionally during the preparation of isoflavone aglucone.

The extract from soybeans or germs of soybeans used in the present invention was converted into isoflavone aglucone by β-glucosidase, α-glucosidase or pectinase, which suggests that *Rhodotorula glutinis* produces the said enzymes. Concentration of solids in the said extract is preferred to be 8–20 g/l. When the concentration is below 8 g/l, a ratio of conversion is high, and big facilities are, however, required during industrialization, which gives rise to uneconomical results. When it exceeds 20 g/l, the big facilities are not required, and the ratio of conversion by fermentation is, however, low.

Seed culture was carried out by culturing a strain stored in a frozen state in a potato dextrose medium on a shaking incubator. For main culture, an extract of soybeans or germs of soybeans was used as a medium in an early stage of fermentation. During the fermentation, a stirring rate was adjusted to 300–600 rpm, and air was controlled to be 0.5–2.5 vvm. When pH falls below 4.0, growth of the strain is slow and the productivity is low. When pH exceeds 8.0, growth of the strain is allowed and enzyme activities, however, decrease to result in a low ratio of conversion. Time for culture is preferably 30–54 hours.

During the fermentation, content of dissolved oxygen was measured employing a dissolved oxygen electrode of polarographic type (Ingold, Swiss). Stirring rate was adjusted to 350–400 rpm at the beginning of fermentation, and later to 400–600 rpm so that content of the dissolved oxygen may be at least 20%, compared to that of 100% in the early stage of the fermentation, since content of dissolved oxygen decreases during the fermentation. Moreover, air injection was controlled. If content of the dissolved oxygen is lower than 20%, total cell volume decreases.

The concentration of main elements of isoflavone aglucone such as daidzein, glycitein and genistein was measured by an UV detector at the wavelength of 260 nm, employing HPLC (Waters, U.S.A) equipped with SUPELCOSIL LC-18 (SUPELCO, U.S.A) column. In this connection, a mixture of acetonitrile:water:acetic acid was used as a solvent in a ratio of 70:30:0.1, and a flow rate was 1.0 ml/min at room temperature. Cell concentration was determined by measuring turbidity at 600 nm using a turbidimeter and converting into a dry weight using a standard curve previously obtained.

The present invention is further illustrated in the following examples, which should not be taken to limit the scope of the invention.

EXAMPLE 1

Seed culture: A *Rhodotorula glutinis* strain (KCCM-10172) was inoculated in a 250 ml-flask containing 50 ml of potato dextrose medium and cultured at 30° C. on a shaking incubator operating at 240 rpm for 24 hours.

An extract of soybeans or germs of soybeans: Five volume of water was added to soybeans or germs of soybeans isolated in a ratio of 95%, and incubated at 80° C. for 2 hours to extract isoflavone from the germs. In this connection, extraction ratio of isoflavone was 45–50%. In order to increase extraction ratio of isoflavone, extraction was carried out successively three times to obtain extraction ratio of 65–70%. The extract thus obtained was used for further experiments.

Main culture: The cultured medium obtained from seed culture was inoculated in a 250 ml-flask containing 50 ml of the extract, and cultured at 30° C. on a shaking incubator operating at 220 rpm. pH of the medium was adjusted to 5.0 in the early stage of the fermentation and not controlled later. Production of isoflavone aglucone according to culture time was summarized in Table 1. On the sixth day after the culture, production of isoflavone aglucone reached at its maximum.

TABLE 1

Quantity of isoflavone aglucone produced by the isolated strain in a 250 ml-flask according to culture time

| Culture time | Concentration of glucoside (ppm/l) | Concentration of aglucone (ppm/l) | Ratio of conversion (%) | Productivity (ppm/l-day) | Purity (%) |
|---|---|---|---|---|---|
| 0 | 100 | 0.50 | 0 | 0 | 0 |
| 2 | 73 | 15 | 30 | 7.5 | 17 |
| 4 | 42 | 27 | 54 | 6.75 | 39 |
| 5 | 25 | 38 | 76 | 7.6 | 60 |
| 6 | 0 | 48.0 | 96 | 8.0 | 100 |

Ratio of conversion(%): ((isoflavone aglucone × 2)/isoflavone glucoside) × 100
Productivity (ppm/l-day): isoflavone aglucone (ppm/l)/day
Purity (%): (isoflavone aglucone/isoflavone aglucone + isoflavone glucoside) × 100

EXAMPLE 2

The main culture was carried out in the same manner as in Example 1 except for variation of concentration of the extract, and the results of culture for 6 days (144 hours) were summarized in Table 2.

TABLE 2

Quantity of isoflavone aglucone produced in a 250 ml-flask according to concentration of the extract

| Concentration of solid in the extract (g/l) | Early concentration of glucoside (ppm/l) | Aglucone (ppm/l) | Ratio of conversion | Productivity | Purity |
|---|---|---|---|---|---|
| 5 | 1150 | 525 | 91.3 | 3.65 | 84.0 |
| 10 | 1980 | 912 | 92 | 6.3 | 85.4 |

TABLE 2-continued

Quantity of isoflavone aglucone produced in a 250 ml-flask according to concentration of the extract

| Concentration of solid in the extract (g/l) | Early concentration of glucoside (ppm/l) | Aglucone (ppm/l) | Ratio of conversion | Productivity | Purity |
|---|---|---|---|---|---|
| 20 | 4050 | 1850 | 91.3 | 12.85 | 84.1 |
| 25 | 4550 | 1550 | 68.1 | 10.76 | 51.6 |

Ratio of coversion(%): ((isoflavone aglucone × 2)/isoflavone glucoside) × 100
Productivity (ppm/l-hr): isoflavone aglucone (ppm/l)/hour
Purity (%): (isoflavone aglucone/isoflavone aglucone + isoflavone glucoside) × 100

EXAMPLE 3

Seed culture was carried out in the same manner as in Example 1, and the main culture was performed in a condition of aeration of 1.0 vvm and stirring rate of 350 rpm at 30° C. for 48 hours under various pH conditions, using an extract in a solid concentration of 10% as a medium and a 15 l-fermenter containing 10 l of the medium. The results were shown in Table 3 below.

TABLE 3

Quantity of isoflavone aglucone produced in a 15 l-fermenter according to pH

| Ph | Early concentration of glucosides (ppm/l) | Aglucone (ppm/l) | Ratio of conversion | Productivity | Purity |
|---|---|---|---|---|---|
| 3.0 | 1980 | 300 | 30 | 6.25 | 17.9 |
| 5.0 | | 470 | 47 | 9.79 | 31.1 |
| 7.0 | | 430 | 43 | 8.96 | 27.7 |
| 9.0 | | 310 | 31.3 | 8.33 | 18.6 |

Ratio of conversion(%): ((isoflavone aglucone × 2)/isoflavone glucoside) × 100
Productivity (ppm/l-hr): isoflavone aglucone (ppm/l)/hour
Purity (%): (isoflavone aglucone/isoflavone aglucone + isoflavone glucoside) × 100

EXAMPLE 4

Fermentation was carried out in a condition of aeration of 1.0 vvm and stirring rate of 350 rpm for 48 hours in the same manner as in Example 3 except in a condition of optimum pH of 5.0 at various temperatures. The results were shown in Table 4 below.

TABLE 4

Quantity of isoflavone aglucone produced in a 15 l-fermenter according to temperature

| Temperature (° C.) | Early concentration of glucosides (ppm/l) | Aglucone (ppm/l) | Ratio of conversion | Productivity | Purity |
|---|---|---|---|---|---|
| 20 | 1980 | 350 | 35.4 | 7.29 | 21.4 |
| 25 | | 480 | 48.5 | 10.0 | 32 |
| 25 | | 500 | 50.5 | 10.41 | 33.8 |
| 35 | | 320 | 32.3 | 6.67 | 19.3 |
| 40 | | 200 | 20.2 | 4.16 | 11.2 |

EXAMPLE 5

In the optimum condition thus selected, quantity of isoflavone aglucone produced according to culture time was examined in order to find out the culture time when the ratio of conversion reaches the maximum value. Fermentation was carried out in a 15 l-fermenter containing 10 l of the extract in a solid concentration of 10%, and content of dissolved oxygen was adjusted to 20% or more by controlling the stirring rate to be 300 –600 rpm. During the fermentation, pH was adjusted to 5.0 and the temperature for culture was 30° C. Quantity of isoflavone aglucone produced according to culture time was summarized in Table 5. Thus, isoflavone (aglucone purity of 90% more) in the form of aglucone was obtained from isoflavone existing in the form of glucoside within the extract, by fermentation.

TABLE 5

Quantity of aglucone produced from 10 l of the extract in a 15 l-fermenter according to culture time

| Time | Concentration of glucosides (g/l) | Concentration of aglucone (ppm/l) | Ratio of conversion | Productivity | Purity |
|---|---|---|---|---|---|
| 0 | 2000 | 0 | — | — | — |
| 6 | 2000 | 0 | — | — | — |
| 12 | 1800 | 50 | 5 | 4.16 | 0.02 |
| 18 | 1150 | 500 | 50.2 | 27.8 | 30.4 |
| 24 | 900 | 550 | 55 | 22.9 | 37.9 |
| 30 | 500 | 700 | 70 | 23.3 | 58.3 |
| 36 | 240 | 850 | 85 | 23.61 | 78.0 |
| 42 | 50 | 970 | 97 | 23.10 | 95.1 |
| 48 | 0 | 900 | 90 | 18.75 | 100 |
| 54 | 0 | 760 | 76 | 14.07 | 100 |

EXAMPLE 6

The conversion ratio of *Rhodotorula glutinis* of the invention was compared with those of the conventional ones. In this connection, the same extract in the early glucoside concentration of 1980 ppm/l was used. In accordance with the invention, fermentation was carried out for 40 hours and the results were shown in Table 6.

TABLE 6

Quantity of aglucone produced from 10 l of the extract in a 15 l-fermenter according to culture time

| Strain | Concentration of aglucone (ppm/l) | Ratio of conversion | Productivity | Purity |
|---|---|---|---|---|
| KCCM-50262 (ATCC-2527) | 810 | 81 | 20.25 | 69.2 |
| KCCM50531 (IFO1501) | 780 | 78 | 19.5 | 65.0 |
| KCCM50528 (IFO1 099) | 790 | 79 | 19.75 | 66.4 |
| KCCM-10172 | 970 | 97 | 24.5 | 96.0 |

As clearly illustrated and demonstrated as the above, for the preparation of isoflavone in the form of isoflavone aglucone by removing glucoside from isoflavone glycoside, use of a novel *Rhodotorula glutinis* strain resulted in the same results in the light of ratio of conversion and productivity, compared with the conventional *Aspergillus* and *Lactobacillus* strains, and resulted in a good ratio of conversion, compared with the conventional *Rhodotorula glutinis*.

In addition, *Rhodotorula glutinis* of the invention isolated from fermented soybeans is a strain generated during fermentation to make the fermented soybeans playing a role as a material for soybean paste and soy sauce made in Korea, and harmless to human in contrast to the conventional *Rhodotorula glutinis* strains. Moreover, an animal experiment confirmed that isoflavone aglucone prepared by *Rhodotorula glutinis* of the invention in accordance with the invention showed no acute, subacute and chronic toxicity.

Although the foregoing invention has been described in detail by way of illustration and examples for purposes of clarity and understanding, it will be obvious that certain changes and modifications may be practiced within the scope of the invention, as limited only by the scope of the appended claims.

What is claimed is:

1. A process for preparing isoflavone aglucone of a high purity, the process comprising:

preparing a culture of *Rhodotorula glutinis* (deposited with the Korean Culture Center of Micro-organisms as deposition No. KCCM- 0172) isolated from fermented soybeans;

preparing an extract of soybeans or germs of soybeans as a nutrient and substrate of the culture; and culturing the culture with the extract.

2. The process for preparing isoflavone aglucone of claim 1, wherein the culture was carried out in a condition of pH 4.0–8.0.

3. The process for preparing isoflavone aglucone of claim 1, wherein the culture was carried out at a temperature of 25–35° C.

4. The process for preparing isoflavone aglucone of claim 1, wherein the culture was carried out for 30–54 hours.

5. The process for preparing isoflavone aglucone of claim 1, wherein content of dissolved oxygen is maintained to be at least 20% during the culture against that in the early stage of the fermentation to obtain isoflavone aglucone showing a purity of 90% or more.

* * * * *